(12) United States Patent
Berg

(10) Patent No.: US 7,513,252 B2
(45) Date of Patent: Apr. 7, 2009

(54) METHOD AND ARRANGEMENT FOR SCAVENGING ESCAPE GAS

(76) Inventor: Hakan Berg, Kungsportsavenyn 30, Goteborg (SE) S-411 36

( * ) Notice: Subject to any disclaimer, the term of this patent is extended or adjusted under 35 U.S.C. 154(b) by 496 days.

(21) Appl. No.: 10/711,894

(22) Filed: Oct. 12, 2004

(65) Prior Publication Data
US 2006/0076013 A1 Apr. 13, 2006

(51) Int. Cl.
*A61M 15/00* (2006.01)
*A61M 16/10* (2006.01)
(52) U.S. Cl. .............................. 128/203.12; 128/205.12; 128/205.23; 128/203.22; 128/205.25; 128/205.27; 128/205.29; 128/204.18; 128/910; 128/912
(58) Field of Classification Search ............ 128/205.12, 128/205.23, 205.27, 205.29, 203.12, 203.22, 128/205.25, 206.27, 206.29, 204.18, 910, 128/912
See application file for complete search history.

(56) References Cited

U.S. PATENT DOCUMENTS 4,015,598 A * 4/1977 Brown .................... 128/205.25

* cited by examiner

*Primary Examiner*—Patricia Bianco
*Assistant Examiner*—Nihir Patel
(74) *Attorney, Agent, or Firm*—Novak Druce + Quigg, LLP

(57) ABSTRACT

Method and device for scavenging tainted escape gas at a location proximate the patient's mouth (24) before that gas diffuses into, or otherwise reaches the personal breathing space (32, 35) of attending health care providers (38, 39). The scavenging device (50) includes, but is not limited to a suction arrangement (52) suspendable from a patient's nasal mask (40) used for administering gaseous analgesia or anesthetic such as nitrous oxide to the patient (20). A suction inlet (54) is positionable proximate the patient's mouth (24) and an exhaust outlet (56) is provided that is interconnectable with a vacuum source (46).

36 Claims, 7 Drawing Sheets

METHOD AND ARRANGEMENT FOR SCAVENGING ESCAPE GAS

TECHNICAL FIELD

The present invention relates to devices for improving air quality conditions for health care providers; more particularly, the invention relates to methods and devices for scavenging away escape gas about a patient that contains gaseous analgesia or anesthetic thereby preventing the care provider's exposure thereto.

BACKGROUND ART

It is well documented that persons can suffer negative consequences from exposure to certain analgesia and/or anesthetic gases; and particularly, nitrous oxide. The administration of nitrous oxide to patients is especially popular during dental procedures. The relatively short periods that the patient is exposed to the gas is generally accepted as being tolerable from a health perspective. A by-product of the administration of such gases, however, particularly during dental procedures in which the patient's mouth remains open and uncovered is a leakage of the administered gas into the care provider's breathing space from the patient's open mouth. Depending on the fit of the nasal mask against the patient's face, it is also possible for some leakage to occur thereabout while gas is administered.

The adverse health effects of exposure to low levels of nitrous oxide have been demonstrated in epidemiologic and laboratory studies. The effects range from those of the more bothersome type including irritability, headache, and nausea to the more severe including congenital abnormalities, spontaneous abortion, infertility, lymphoid malignancies, cervical cancer, and hepatic, renal and neurological disease.

In an effort to continue patient benefits from the administration of nitrous oxide, while minimizing, if not alleviating the negative effects upon the care providers, several air evacuation devices have been developed. One example is found in International Patent Application Number PCT/CA95/00504 in which a system entitled Ventilation of Medical Gases is described. The intake portions of this device, however, are positioned against each of the patient's cheeks in a space that the care provider may wish to occupy, or at least have clear during medical procedures, and especially dental procedures. Still further, the positioning of the intakes which are supported on, and substantially cover the patient's cheek areas can prove to be a disturbance to the patient.

Another attempted solution is found in International Patent Application Number PCT/SE89/00213 entitled Mouth Piece for Suction of Exhaled Air. This device is described as having wing members that are intended to be brought into the mouth of the patient and which rest upon the inner side of the mouth cavity. The facial and inner-mouth contact that this device requires also creates a disturbance for the patient which is desirably avoided.

Taking these exemplarily, but inadequate solutions into consideration, the need for improved and alternative methods has been recognized. Goals for such replacement options include patient comfort and effectiveness for minimizing care provider exposure to escape gas.

DISCLOSURE OF INVENTION

The primary reason for utilizing the presently disclosed invention(s) is to provide protection to attending health care providers from harmful exposure to the detrimental affects of leaked analgesia and/or anesthetic gases, of which nitrous oxide serves as an example.

Another goal and benefit of the present invention(s) is to provide as much comfort and as little disturbance to the patient as possible.

Still another goal is to facilitate the scavenging of analgesia and/or anesthetic tainted escape gas, while also providing the health care provider a means by which to keep the working space directly adjacent the patient's mouth clear for performing needed procedures.

As will be described in greater detail hereinbelow, one embodiment of the present invention takes the form of a device for scavenging tainted escape gas at a location proximate the patient's mouth before that gas diffuses into, or otherwise reaches the personal breathing space of attending health care provider(s). The scavenging device includes, but is not limited to a suction arrangement suspendable from a patient's nasal mask used for administering gaseous analgesia or anesthetic to the patient. A suction inlet is positionable proximate the patient's mouth and an exhaust outlet is interconnectable with a vacuum source.

In an alternative embodiment, the invention takes the form of a method for scavenging tainted escape gas released into the personal breathing space of a health care provider while performing a medical procedure on a patient receiving a gaseous analgesia or anesthetic. The method includes suspending a suction arrangement from a patient's nasal mask used for administering gaseous analgesia or anesthetic to a patient. A suction inlet of the suction arrangement is positioned proximate the patient's mouth for scavenging tainted escape gas released into the personal breathing space of a health care provider when the health care provider is positioned adjacent the patient's head. An exhaust outlet of the suction arrangement is interconnected to a vacuum source and tainted escape gas scavenging is instituted proximate the patient's face thereby benefiting the health care provider by limiting exposure of the health care provider to tainted escape gas.

MODE FOR INVENTION

Figure 1:
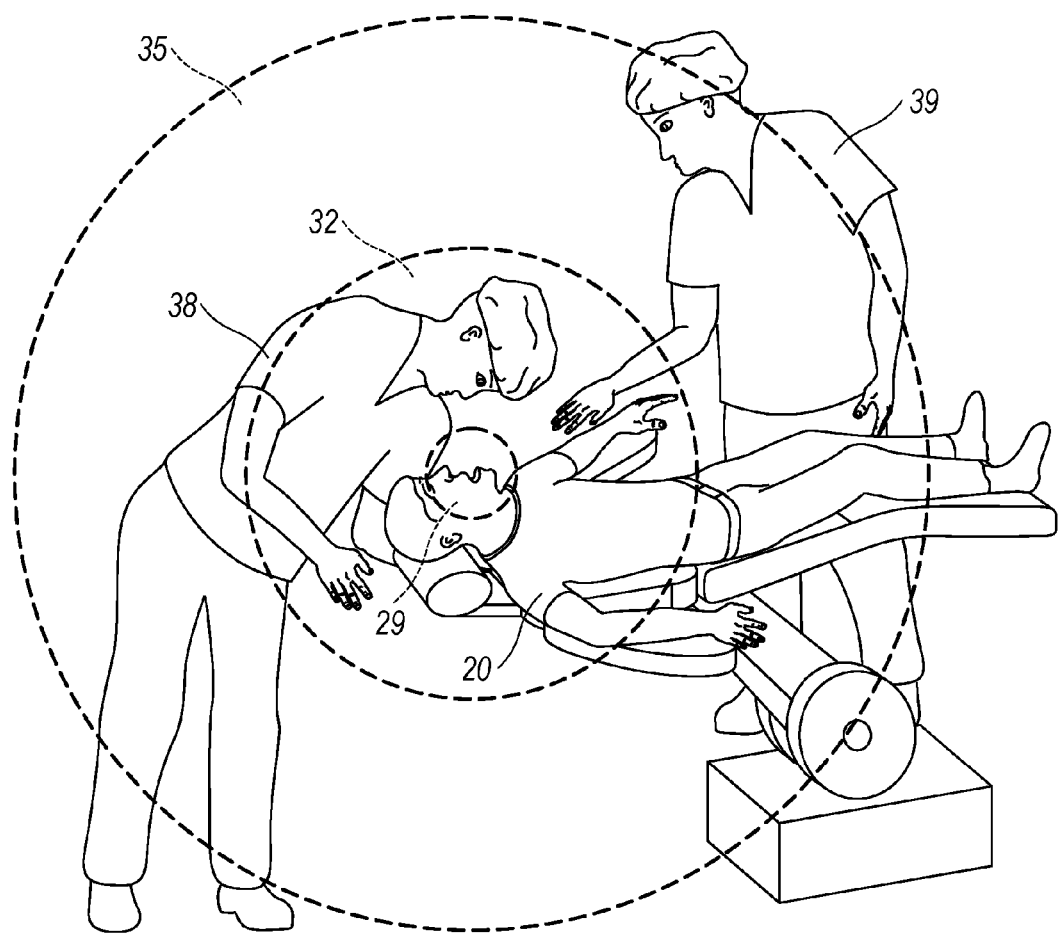
FIG. 1 is a perspective view schematically illustrating, on a radial basis, breathing zones of two health care providers and an escape gas cloud zone of a dental patient exemplarily receiving nitrous oxide during an oral treatment procedure.
Figure 2:
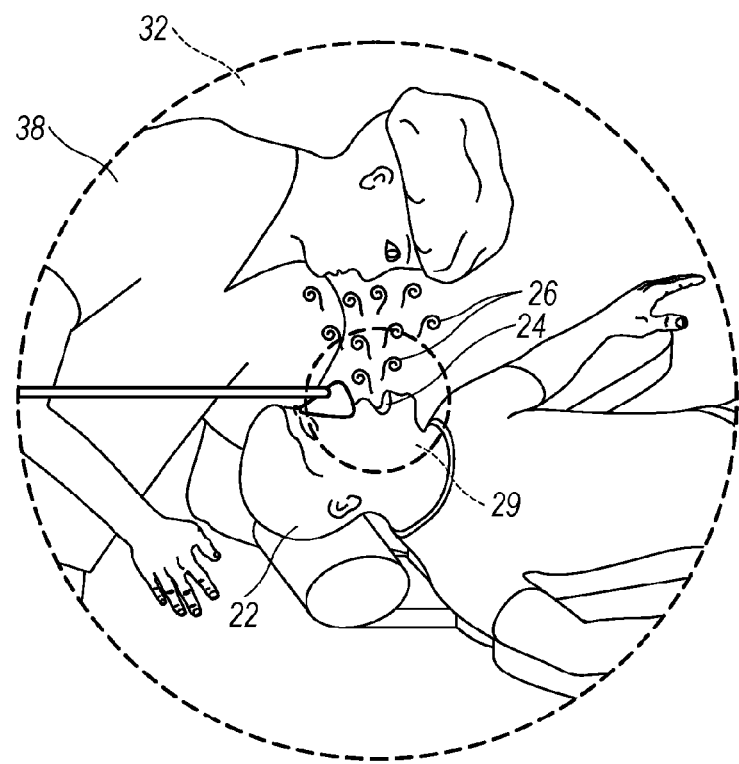
FIG. 2 is a cropped perspective view from FIG. 1 showing the diffusion of tainted escape gas as it primarily emanates from the patient's mouth into the personal breathing space of the closer care giver.
Figure 3:
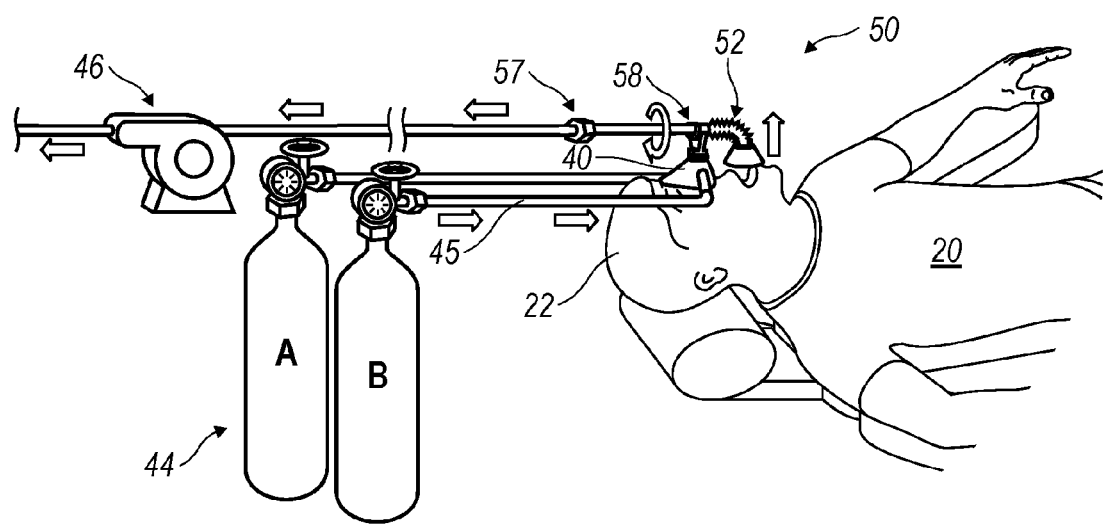
FIG. 3 is a schematic view of one device configured according to the teachings of the present invention, including gas supply and vacuum source, installed upon a patient.

FIGS. 1 and 2 demonstrate environments in which the present invention(s) may be advantageously utilized. FIG. 1 shows the general environment of an operatory in which medical procedures, including dental procedures, are typically performed. A patient 20 is shown in a reclined position. A first health care provider 38 is shown proximate the patient's head 22, and could exemplarily be a dentist conducting an oral procedure on the patient 20. A second health care provider 39 is shown adjacent the patient 20 (close by, and in the direct vicinity, but not as close to the patient's head 22 as the proximate health care provider 38), and could exemplarily be a dental assistant providing support to the dentist 38 during an oral procedure.

In FIG. 2, the patient 20 is receiving a gaseous analgesia or anesthetic from a nasal mask 40 through a gas supply conveyance 45 from an appropriate gas source 44. Because the patient's mouth 24 is necessarily open for the medical (oral) procedure being conducted, tainted escape gas 26 exhalation and bleed-through supplied gas 44 is released into the personal breathing space 32, 35 of the proximately and adjacently located health care providers 38, 39 before, during and after the performance of the medical procedure on the patient 20 receiving gaseous analgesia or anesthetic through a nasal mask 40.

FIG. 2 also demonstrates the diffusive nature of the tainted escape gas 26. A highest concentration zone 29 is shown immediately about the patient's 20 open mouth 24. Radiating thereabout is first a high concentration zone 32 defined to encompass the personal breathing space 32 of the proximately located health care provider 38. Radiating still further out is a second, moderate concentration zone 35 defined to encompass the personal breathing space 35 of the adjacently located health care provider 39. Without the remedial measures prescribed by the present inventions, it is well appreciated in the literature (it is known) that typical concentrations of unscavenged escape gas (particularly nitrous oxide) in these zones 32, 35 can be harmful to health care providers that are subjected to repeated and/or prolonged periods of exposure.

FIGS. 1 and 2 graphically demonstrate an exemplary environment for the utilization of the instantly disclosed invention(s).

A first and primary embodiment of the present invention, with minor modifications therebetween, is depicted in FIGS. 3-6 wherein the inventive arrangement takes the form of a device for scavenging tainted escape gas 26 at a location proximate the patient's mouth 24 before it diffuses into, or otherwise reaches the personal breathing space 32, 35 of attending health care provider(s) 38, 29 who are performing a medical procedure on a patient 20 that is receiving a gaseous analgesia or anesthetic.

In this embodiment, the scavenging device 50 comprises (includes, but is not necessarily limited to) a suction arrangement 52 that constitutes a suction means and is suspendable (configured to be, but not yet suspendedly installed in this description—see FIGS. 11 and 12 demonstrating the concept of being suspendable, but not get suspended) from a patient's nasal mask 40 used for administering gaseous analgesia or anesthetic to the patient 20. The suction arrangement 52 has a suction inlet 54 positionable proximate the patient's mouth 24 for scavenging tainted escape gas 26 released from the patient's mouth 24, and with the potential for diffusing into the personal breathing space 32, 35 of one or more of the health care providers 38, 39 when the health care provider is positioned proximate and/or adjacent the patient's head, respectively. The suction arrangement further includes an exhaust outlet 56 interconnectable (but not necessarily presently connected unless specifically recited) utilizing a quick-style connection 57 with a vacuum source 46 for instituting tainted escape gas 26 scavenging proximate the patient's face (near the face, and preferably close to the mouth 24) for the benefit of the health care provider(s) 38, 39 by limiting exposure of the health care provider to tainted escape gas 26.

In a complementary development of the scavenging device, an adjustable interconnection 58 is further included that is configured to mount the suction arrangement 52 to the patient's nasal mask 40. The adjustable interconnection 58 is configured to enable variable positioning of the suction inlet 54 relative to the patient's mouth 24. It should be appreciated that various exemplary embodiments for the interconnector 58 are shown at least in FIGS. 5, 8, 9 and 11.

Another embodiment of the present invention couples the adjustable interconnection 58 upon the patient's nasal mask 40 (as opposed to merely been suspendable thereupon) and thereby mounts the suction arrangement 52 on the nasal mask 40. The adjustable interconnection enables variable positioning of the suction inlet 54 relative to the patient's mouth 24.

The mounting of the suction arrangement 52 upon the patient's nasal mask 40 is preferably an exclusive point-of-suspension 62 of the suction arrangement 52 substantially from the nose of the patient 20, downward (from where the nasal mask 40 rests in contact with the patient 20).

Regarding these several embodiments, the suction arrangement 52 and the mounting 58 together establish a cantilever suspension 60 of the suction inlet 54 below the nose of the patient 20.

Figure 4:
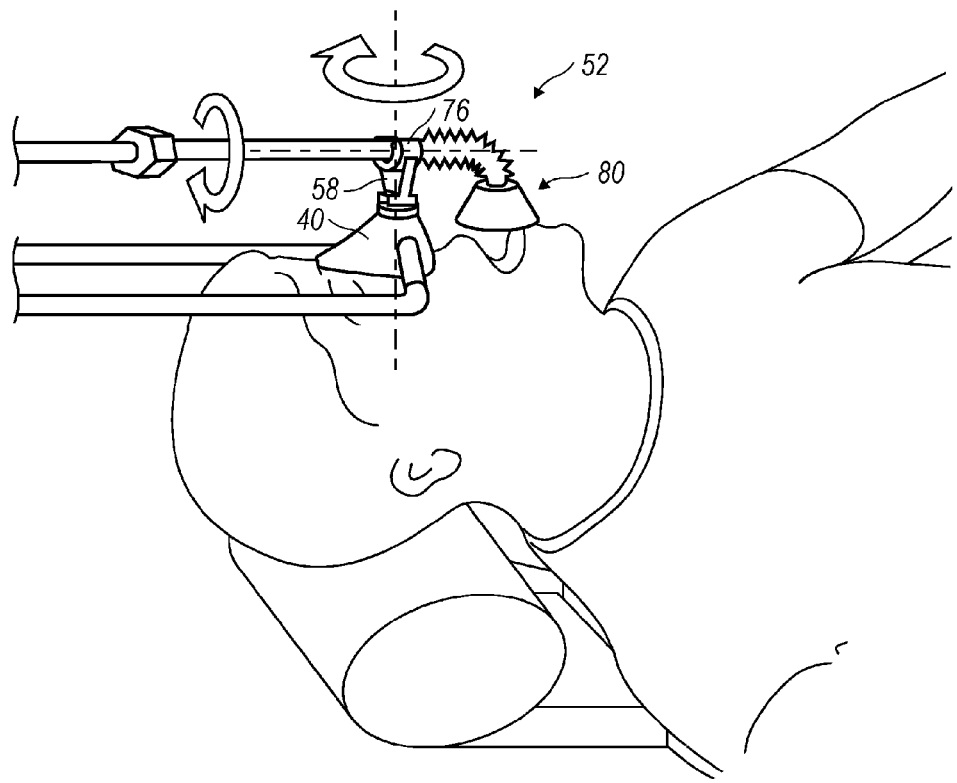
FIG. 4 is a detailed view of the portion of the arrangement depicted in FIG. 3 proximate the patient's face.
Figure 5:
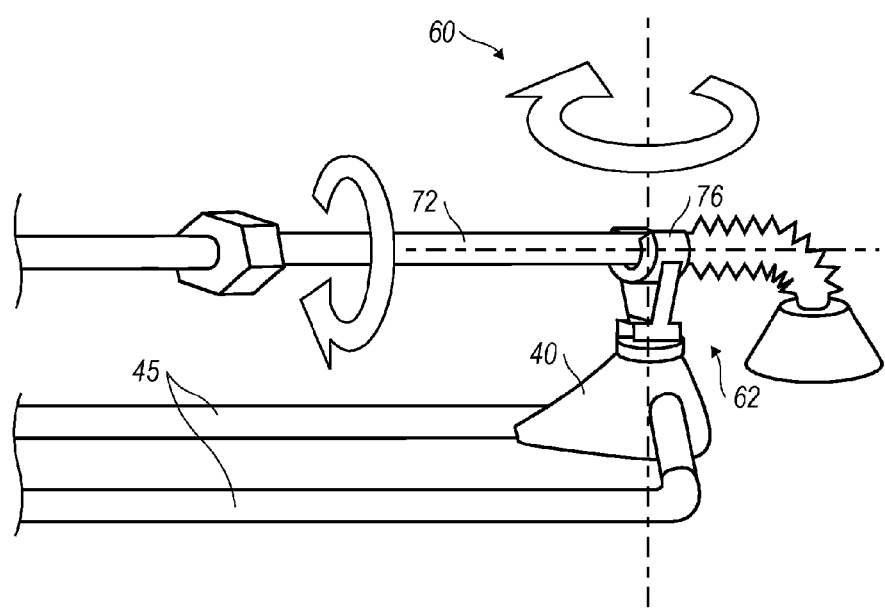
FIG. 5 is a detailed view of the suction arrangement depicted in FIG. 3, rotatably interconnected to the nasal mask.
Figure 6:
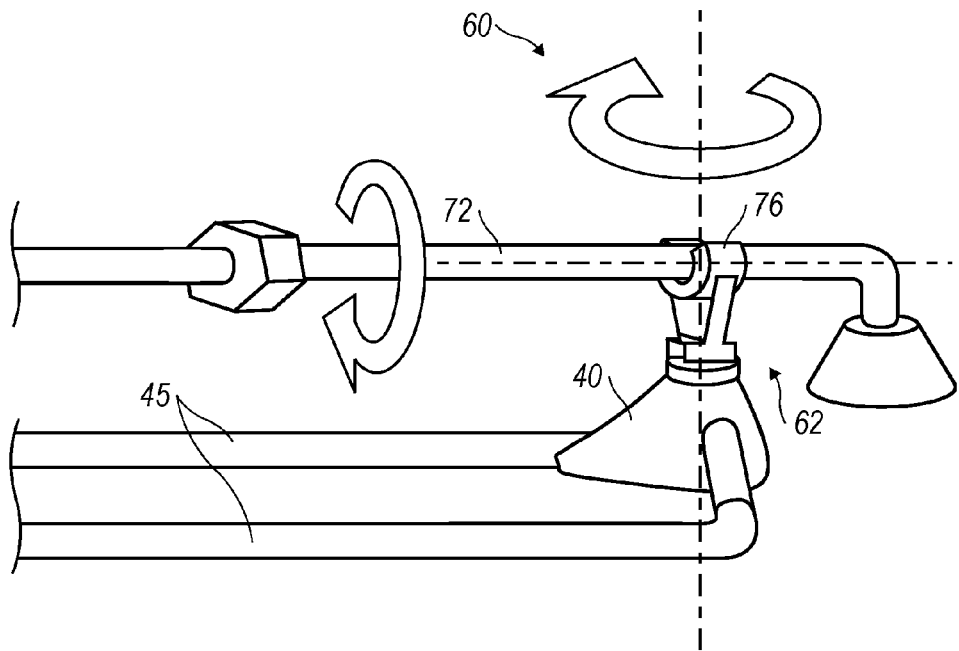
FIG. 6 is a detailed view of the suction arrangement depicted in FIG. 3, but instead of a corrugated curved portion, a fixed curved portion is utilized instead.
Figure 7:
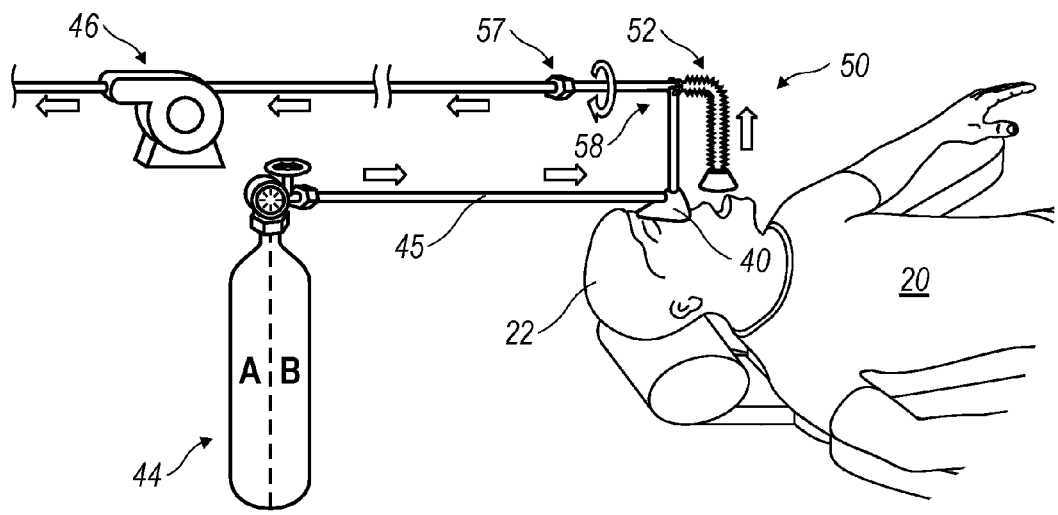
FIG. 7 is a perspective view of an alternative arrangement to that depicted in FIG. 3.
Figure 8:
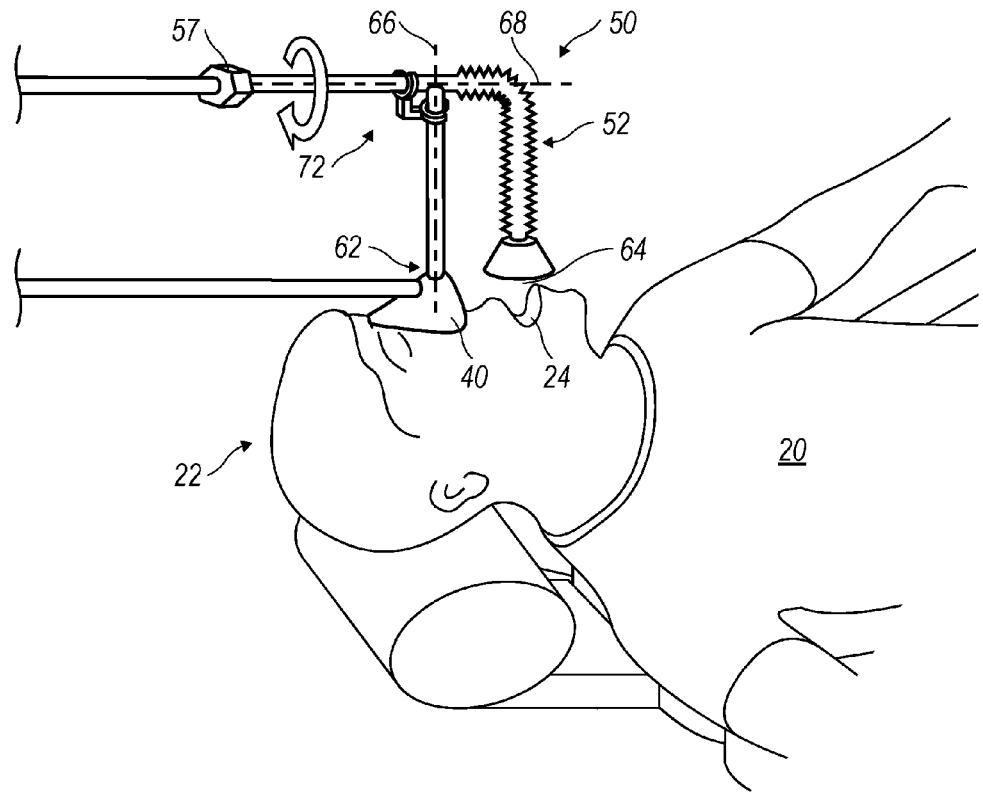
FIG. 8 is a perspective view of yet another alternative arrangement to that depicted in FIG. 3.

The cantilever suspension 60 establishes a clearance space 64 proximate the patients mouth 24 for facilitating procedures conducted adjacent to, and inside the patient's mouth 24 by the health care provider(s) 38, 39 as exemplarily represented in FIGS. 4 and 8.

As clearly depicted in FIGS. 5, 6, 7, 9 and 10, the suction arrangement 52 can be supported in a mounting (adjustable interconnection) 58 that facilitates pivotation and/or rotation of the suction arrangement 52 about an axis 68 oriented transverse (not parallel) to a face-forward direction 66 of the patient's nasal mask 40 when fitted upon a patient 20.

While the possibility of any transverse orientation is contemplated, it is preferred that the mounting 58 facilitates rotation of the suction arrangement about an axis 68 oriented substantially perpendicular to a face-forward direction 66 of the patient's nasal mask 40 when fitted upon a patient 20.

Figure 11:
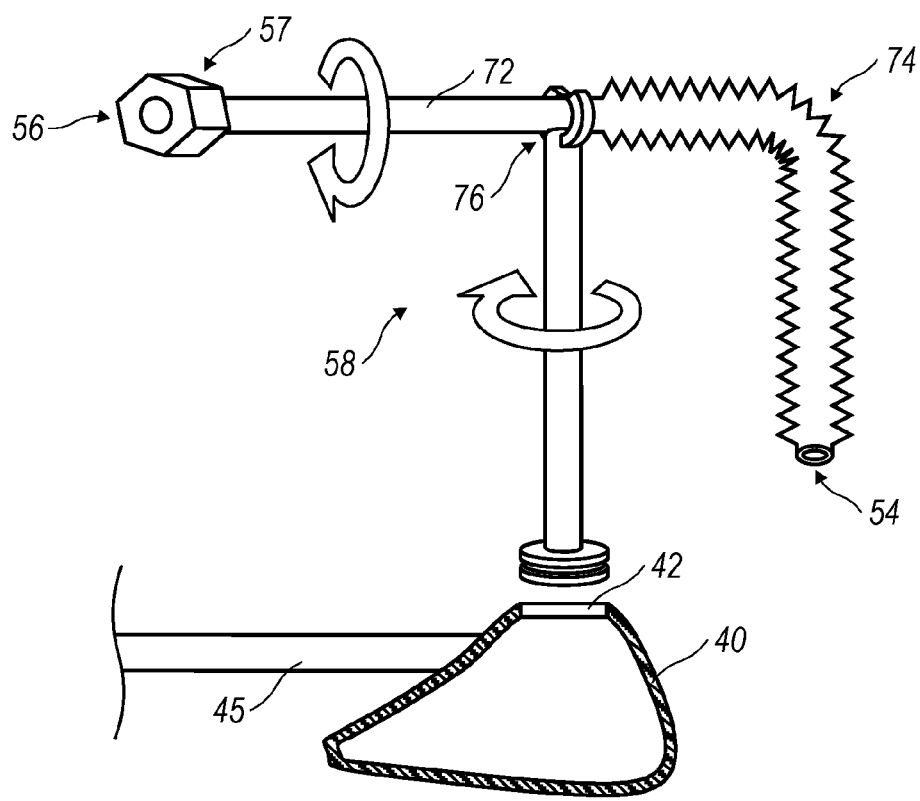
FIG. 11 is a detailed view of the elongate tubular extension of FIG. 10 clip-secured in a top end of a substantially vertical interconnection member, for rotation about a substantially horizontal axis, and with the interconnection member being mounted to the nasal mask in an orifice provided therein.

In the embodiments of the invention depicted in FIGS. 4 and 11, the scavenging device 50 includes a mounting that facilitates pivotation (rotation) of the suction arrangement about the axis 66 oriented substantially parallel to a face-forward direction of the patient's nasal mask 40 when fitted upon the patient 20. This capability alone is considered an embodiment of the invention(s), but its combination with the immediately above described capability for pivotation and/or rotation of the suction arrangement 52 about the axis 68 also constitutes an embodiment of the invention(s).

In the exemplary embodiments of FIGS. 4 and 11, the mounting 58 is secured in an aperture 42 provided in the patient's nasal mask 40. As described hereinabove, certain nasal masks presently available on the market provide such an aperture 42 which serves as an exhaust aperture for others who directly connect a vacuum means thereto, primarily for the benefit of the patient.

Figure 12:
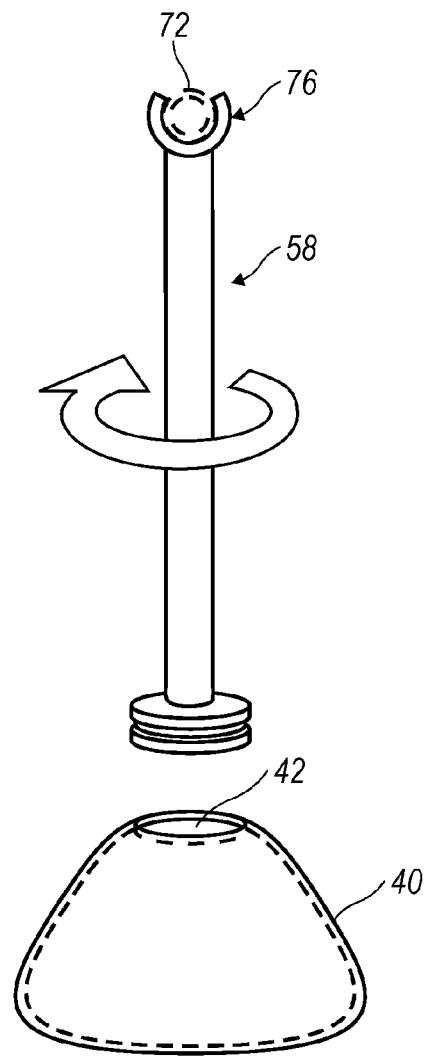
FIG. 12 is an exploded perspective view of select components of the embodiment of the arrangement depicted in FIG. 11.

A lower portion of the mounting 58 is spool-shaped, and the mounting 58 can be rotatably seated in the aperture 42 for facilitating pivotation and/or rotation of the suction arrangement 52 about an axis 66 oriented substantially parallel to the face-forward direction of the patient's nasal mask 40 (see exemplarily FIGS. 11 and 12). The nasal mask is typically constructed from a flexible plastic or rubber (natural or synthetic) based material; therefore, an advantageously dimensioned aperture 42 will fit snuggly about the spindle portion of the spool-shaped mounting between upper and lower flanges formed thereby as depicted most clearly in FIGS. 11 and 12.

Figure 9:
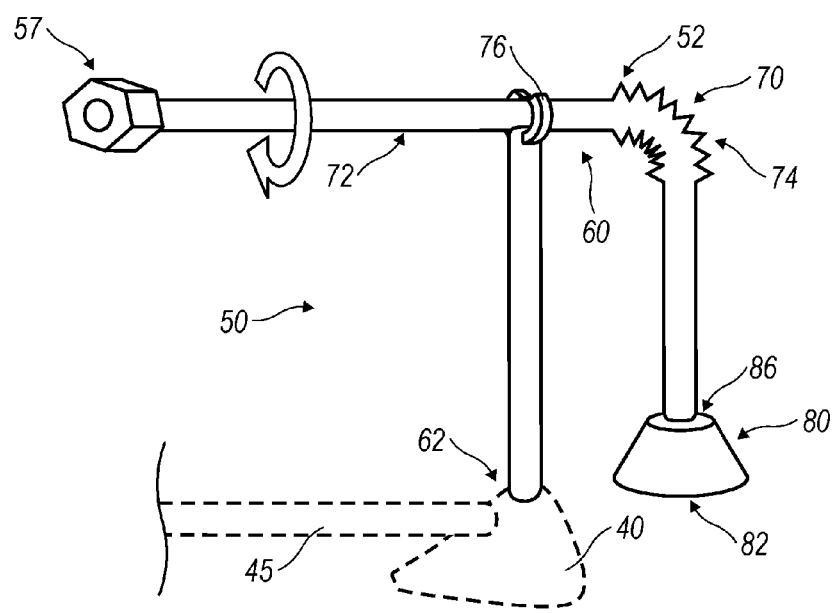
FIG. 9 is a perspective view of still a further embodiment of the suction arrangement interconnected to and nasal mask, which is shown in phantom.
Figure 10:
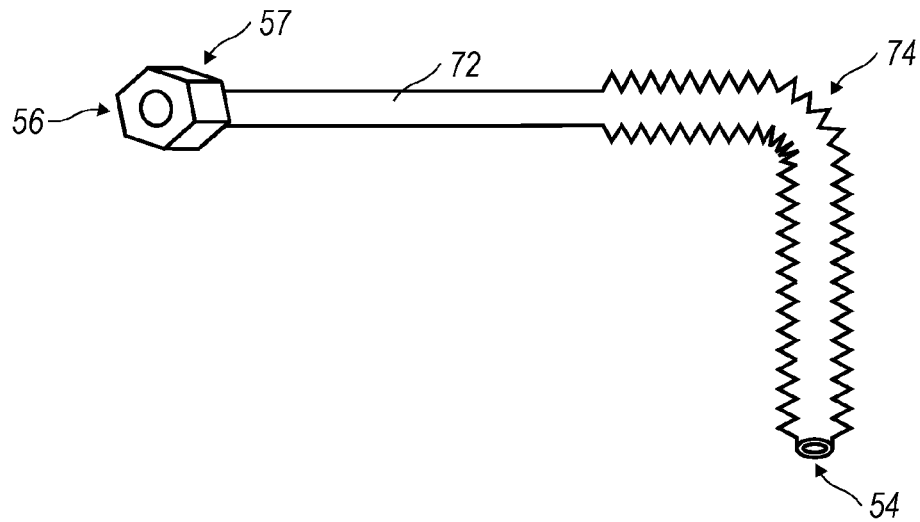
FIG. 10 is a semi-schematic perspective view of an exemplary elongate tubular portion in which the distal end is corrugated along a substantial entirety thereof.

As illustrated between FIGS. 9 and 10, one embodiment of the presently disclosed invention(s) is exclusively constituted by the suction arrangement 52 alone and which comprises an elongate tubular extension 70 that is configured to project from the mounting (preferably, releasably held therein) and terminating at a distal end of the extension 70 in the suction inlet 54. When in use, the suction inlet 54 is suspended at a location above the patient's face with a clearance space 64 (see FIG. 8) therebetween.

The elongate tubular extension 70 comprises a substantially straight portion 72 and a curved portion 74 that are interconnected so that the suction inlet 54 is typically offset from a longitudinal axis of the substantially straight portion 72.

Therefore, the curved portion 74 offsets the suction inlet 54 from a central axis 68 of at least the straight portion 72 of the elongate tubular extension 70 at the mounting 58.

As depicted in the several illustrations, the curved portion may optionally be partially constituted (along variable proportions thereof) by a corrugated side wall that maintains an operator-set orientation until reset by an outside influence. By no way of limitation, the reader may appreciate that this portion of the invention can be configured similarly to the goose-neck portion of a traditionally configured soda straw.

In one development, the elongate tubular extension 70 is clip-connected to the mounting 58 with an interference friction fit provided therebetween utilizing an interference fit clip securement 76. The interference friction fit enables variable operator orientation setting of the suction inlet 54 relative to the mounting, the setting being held under the influence of the interference friction fit until reorientation is effected by the operator.

The present invention is intended to enable high-volume evacuation about the patient's face, and particularly adjacent the mouth region. It is contemplated that this rate of vacuum may exemplarily be seventeen thousand liters per hour. In earlier studies, it has been recognized that certain health practitioners will not utilize such high volume evacuation, even when available, because of the disturbing noise that can be created, and often taking the form of an annoying whistling sound. To alleviate such hesitation, one feature of the present invention (and which constitutes an invention in and of itself) provides an inlet nozzle 80 for the suction inlet 54 that has an expanded mouth opening 82 and tapering portion 84 located upstream of the mouth opening 82 toward the elongate tubular extension 70. Exemplarily, and as depicted in at least FIG. 13, the nozzle 80 is exemplarily a frusto-conically shaped nozzle 88. Another exemplary configuration of the nozzle 80 is depicted in FIG. 14, and in which the nozzle 90 is substantially hourglass in shape.

Figure 13:
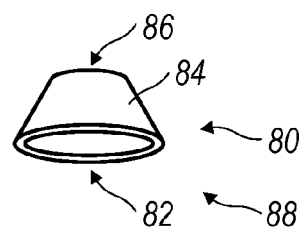
FIG. 13 is a perspective view of a frusto-conically shaped inlet nozzle for the suction arrangement.
Figure 14:
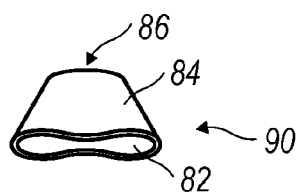
FIG. 14 is a perspective view of an alternative to the device of FIG. 9 depicting an hourglass shaped inlet nozzle for the suction arrangement.

In the example of FIGS. 13 and 14, the nozzle 88 is substantially closed at the top, but is provided with a nozzle-inlet interconnection 86 exemplarily comprising a through aperture for suction communication between the inlet nozzle 80 and the suction inlet 54 of the suction arrangement 52.

In another, but related embodiment, the present invention takes the form of a method for scavenging tainted escape gas released into the personal breathing space of a health care provider while performing a medical procedure on a patient receiving a gaseous analgesia or anesthetic. The method includes suspending a suction arrangement from a patient's nasal mask used for administering gaseous analgesia or anesthetic to a patient. A suction inlet of the suction arrangement is positioned proximate the patient's mouth for scavenging tainted escape gas released into the personal breathing space of a health care provider when the health care provider is positioned adjacent the patient's head. An exhaust outlet of the suction arrangement is interconnected to a vacuum source and tainted escape gas scavenging is instituted proximate the patient's face thereby benefiting the health care provider by limiting exposure of the health care provider to tainted escape gas.

In terms of the method defined immediately above, the mounting of the suction arrangement upon the patient's nasal mask can preferably be an exclusive point-of-suspension of the suction arrangement below the nose of the patient.

In yet another embodiment, an adjustable interconnection configured to mount the suction arrangement to the patient's nasal mask is utilized and that adjustable interconnection enables variable positioning of the suction inlet relative to the patient's mouth.

In still another embodiment, the present invention contemplates adjusting the position of the suction inlet to a side of the patient's mouth thereby facilitating interference-free access thereto by the health care provider (s).

In still yet another embodiment, the suction arrangement is mounted in cantilever suspension from the patient's nasal mask thereby avoiding additional contact with the patient's face, at least below the nose of the patient due to the scavenging of tainted escape gas.

In this regard, it is further contemplated to establish, via utilization of the cantilever suspension, a clearance space proximate the patients mouth for facilitating procedures adjacent and inside the patient's mouth by the health care provider(s).

What is claimed is:

1. A device (50) for scavenging tainted escape gas (26) released from the mouth of a patient (20) receiving a gaseous analgesia or anesthetic into the personal breathing space (32, 35) of a health care provider (38, 29) performing a medical procedure on the patient (20), said device (50) comprising:

a suction arrangement (52) suspendable from a patient's nasal mask (40) used for administering gaseous analgesia or anesthetic to a patient;

said suction arrangement (52) having a suction inlet (54) sufficiently positionable proximate the patient's mouth

(24) so as to scavenge tainted escape gas released from the patient's mouth into the personal breathing space (32, 35) of a health care provider (38, 29) when the health care provider is positioned adjacent the patient (20) and an adjustable interconnection (58) mounting said suction arrangement (52) upon the patient's nasal mask (40), said adjustable interconnection (58) enabling variable positioning of said suction inlet (54) relative to the patient's mouth (24) and said suction arrangement (52) and said mounting (58) together establishing a cantilever suspension (60) of said suction inlet (54) below the nose of the patient (20); and said suction arrangement (52) further comprising an exhaust outlet (56) interconnectable with a vacuum source (46) for instituting tainted escape gas scavenging proximate the patient's face for the benefit of the health care provider by limiting exposure of the health care provider to tainted escape gas (26).

2. The device as recited in claim 1, wherein said mounting of said suction arrangement (52) upon the patient's nasal mask (40) is an exclusive point-of-suspension (62) of said suction arrangement (52) below the nose of the patient (20).

3. The device as recited in claim 1, wherein said cantilever suspension (60) establishes a clearance space (64) proximate the patients mouth (24) for facilitating procedures conducted adjacent to and inside the patient's mouth by the health care provider (38, 39).

4. The device as recited in claim 1, wherein said mounting (58) facilitates pivotation of said suction arrangement (52) about an axis (66) oriented substantially parallel to a face-forward direction of said patient's nasal mask when fitted upon the patient.

5. The device as recited in claim 4, wherein said mounting (58) is secured in an aperture (42) provided in said patient's nasal mask (40), said mounting being rotatable in said aperture (42) for facilitating pivotation of said suction arrangement (52) about an axis (66) oriented substantially parallel to the face-forward direction of said patient's nasal mask.

6. The device as recited in claim 1, wherein said mounting (58) facilitates pivotation of said suction arrangement (52) about an axis (68) oriented transverse to a face-forward direction of said patient's nasal mask when fitted upon a patient.

7. The device as recited in claim 1, wherein said mounting (58) facilitates rotation of said suction arrangement (52) about an axis (68) oriented transverse to a face-forward direction of said patient's nasal mask when fitted upon a patient.

8. The device as recited in claim 1, wherein said mounting (58) facilitates rotation of said suction arrangement (52) about an axis (68) oriented substantially perpendicular to a face-forward direction of said patient's nasal mask when fitted upon a patient.

9. The device as recited in claim 1, said suction arrangement further comprising:

an elongate tubular extension (70) secured at said mounting (58) and terminating at a distal end thereof in said suction inlet (54), said suction inlet (54) being suspended at a location above the patient's face with a clearance space therebetween.

10. The device as recited in claim 9, wherein said elongate tubular extension (70) comprises a substantially straight portion (72) and a remote curved portion (74) that are interconnected so that said suction inlet (54) is offset from a longitudinal axis (68) of said substantially straight portion (72).

11. The device as recited in claim 9, wherein said elongate tubular extension (70) comprises a curved portion (74) that offsets said suction inlet (54) from a central axis (68) of said elongate tubular extension at said mounting (58).

12. The device as recited in claim 10, wherein said curved portion (74) is at least partially constituted by a corrugated side wall that maintains an operator-set orientation until reset by an outside influence.

13. The device as recited in claim 9, wherein said elongate tubular extension (70) is clip-connected to said mounting (58) with an interference friction fit provided therebetween, said interference friction fit enabling variable operator orientation setting of said suction inlet (54) relative to said mounting (58), said setting being held under the influence of said interference friction fit until reorientation is effected by said operator.

14. The device as recited in claim 9, said suction inlet (54) further comprising:

an expanded mouth opening (82) and tapering portion (84) located upstream of said mouth opening (82) toward said elongate tubular extension (70).

15. The device as recited in claim 14, wherein said expanded mouth opening (82) is substantially hourglass shaped (90).

16. The device as recited in claim 14, wherein said expanded mouth opening (82) is substantially frusto-conically shaped (88).

17. A method for scavenging tainted escape gas (26) released from the mouth of a patient (20) receiving a gaseous analgesia or anesthetic into the personal breathing space (32, 35) of a health care provider (38, 39) performing a medical procedure on the patient (20), said method comprising:

suspending a suction arrangement (52) from a patient's nasal mask (40) used for administering gaseous analgesia or anesthetic to the patient;

positioning a suction inlet (54) of said suction arrangement (52) sufficiently proximate the patient's mouth (24) so as to scavenge tainted escape gas released from the patient's mouth into the personal breathing space (32, 35) of a health care provider (38, 39) when the health care provider is positioned adjacent to the patient and adjustably mounting said suction arrangement (52) upon the patient's nasal mask (40) in cantilever suspension (60), said adjustable interconnection (58) enabling variable positioning of said suction inlet (54) relative to the patient's mouth (24); and interconnecting an exhaust outlet (56) of said suction arrangement (52) to a vacuum source (46) and instituting tainted escape gas scavenging proximate the patient's face thereby benefiting the health care provider by limiting exposure of the health care provider to tainted escape gas.

18. The method as recited in claim 17, wherein said mounting of said suction arrangement (52) upon the patient's nasal mask (40) is an exclusive point-of-suspension (62) of said suction arrangement (52) below the nose of the patient.

19. The method as recited in claim 17, further comprising:

adjusting the position of said suction inlet (54) to a side of the patient's mouth (24) thereby facilitating interference-free access thereto by the health care provider.

20. The method as recited in claim 17, further comprising:

establishing, via utilization of said cantilever suspension (60), a clearance space (64) proximate the patients mouth (24) for facilitating procedures adjacent and inside the patient's mouth (24) by the health care provider (38, 39).

21. A device (50) for scavenging tainted escape gas (26) released from the mouth of a patient (20) receiving a gaseous analgesia or anesthetic into the personal breathing space (32, 35) of a health care provider (38, 29) performing a medical procedure on the patient (20), said device (50) comprising:

a suction arrangement (52) comprising a suction means configured for being suspended from a patient's nasal mask (40) used for administering gaseous analgesia or anesthetic to a patient; said suction means having a suction inlet (54) configured to be positioned sufficiently proximate the patient's mouth (24) so as to scavenge tainted escape gas released from the patient's mouth into the personal breathing space (32, 35) of a health care provider (38, 29) when the health care provider is positioned adjacent the patient (20) and an adjustable interconnection (58) mounting said suction arrangement (52) upon the patient's nasal mask (40), said adjustable interconnection (58) enabling variable positioning of said suction inlet (54) relative to the patient's mouth (24) and said suction arrangement (52) and said mounting (58) together establishing a cantilever suspension (60) of said suction inlet (54) below the nose of the patient (20); and said suction means further comprising an exhaust outlet (56) configured to be interconnected with a vacuum source (46) for instituting tainted escape gas scavenging proximate the patient's face for the benefit of the health care provider by limiting exposure of the health care provider to tainted escape gas (26).

22. The device as recited in claim 21, wherein said mounting of said suction arrangement (52) upon the patient's nasal mask (40) is an exclusive point-of-suspension (62) of said suction arrangement (52) below the nose of the patient (20).

23. The device as recited in claim 21, wherein said cantilever suspension (60) establishes a clearance space (64) proximate the patients mouth (24) for facilitating procedures conducted adjacent to and inside the patient's mouth by the health care provider (38, 39).

24. The device as recited in claim 21, wherein said mounting (58) facilitates pivotation of said suction arrangement (52) about an axis (66) oriented substantially parallel to a face-forward direction of said patient's nasal mask when fitted upon the patient.

25. The device as recited in claim 24, wherein said mounting (58) is secured in an aperture (42) provided in said patient's nasal mask (40), said mounting being rotatable in said aperture (42) for facilitating pivotation of said suction arrangement (52) about an axis (66) oriented substantially parallel to the face-forward direction of said patient's nasal mask.

26. The device as recited in claim 21, wherein said mounting (58) facilitates pivotation of said suction arrangement (52) about an axis (68) oriented transverse to a face-forward direction of said patient's nasal mask when fitted upon a patient.

27. The device as recited in claim 21, wherein said mounting (58) facilitates rotation of said suction arrangement (52) about an axis (68) oriented transverse to a face-forward direction of said patient's nasal mask when fitted upon a patient.

28. The device as recited in claim 21, wherein said mounting (58) facilitates rotation of said suction arrangement (52) about an axis (68) oriented substantially perpendicular to a face-forward direction of said patient's nasal mask when fitted upon a patient.

29. The device as recited in claim 21, said suction arrangement further comprising:
an elongate tubular extension (70) secured at said mounting (58) and terminating at a distal end thereof in said suction inlet (54), said suction inlet (54) being suspended at a location above the patient's face with a clearance space therebetween.

30. The device as recited in claim 29, wherein said elongate tubular extension (70) comprises a substantially straight portion (72) and a remote curved portion (74) that are interconnected so that said suction inlet (54) is offset from a longitudinal axis (68) of said substantially straight portion (72).

31. The device as recited in claim 29, wherein said elongate tubular extension (70) comprises a curved portion (74) that offsets said suction inlet (54) from a central axis (68) of said elongate tubular extension at said mounting (58).

32. The device as recited in claim 30, wherein said curved portion (74) is at least partially constituted by a corrugated side wall that maintains an operator-set orientation until reset by an outside influence.

33. The device as recited in claim 29, wherein said elongate tubular extension (70) is clip-connected to said mounting (58) with an interference friction fit provided therebetween, said interference friction fit enabling variable operator orientation setting of said suction inlet (54) relative to said mounting (58), said setting being held under the influence of said interference friction fit until reorientation is effected by said operator.

34. The device as recited in claim 29, said suction inlet (54) further comprising:
an expanded mouth opening (82) and tapering portion (84) located upstream of said mouth opening (82) toward said elongate tubular extension (70).

35. The device as recited in claim 34, wherein said expanded mouth opening (82) is substantially hourglass shaped (90).

36. The device as recited in claim 34, wherein said expanded mouth opening (82) is substantially frusto-conically shaped (88).

* * * * *